US009012862B2

(12) United States Patent
Lin et al.

(10) Patent No.: US 9,012,862 B2
(45) Date of Patent: Apr. 21, 2015

(54) MATERIAL AGING TEST APPARATUS AND METHOD THEREOF

(71) Applicant: Industrial Technology Research Institute, Hsin-Chu (TW)

(72) Inventors: Yi-Wei Lin, Yunlin County (TW); Yu-Tai Li, Taichung (TW); Hung-Sen Wu, Taoyuan (TW)

(73) Assignee: Industrial Technology Research Institute, Hsin-Chu (TW)

( * ) Notice: Subject to any disclaimer, the term of this patent is extended or adjusted under 35 U.S.C. 154(b) by 0 days.

(21) Appl. No.: 14/031,452

(22) Filed: Sep. 19, 2013

(65) Prior Publication Data

US 2014/0084176 A1 Mar. 27, 2014

(30) Foreign Application Priority Data

Sep. 21, 2012 (TW) .............................. 101134832 A
Aug. 2, 2013 (TW) .............................. 102127796 A

(51) Int. Cl.
| | | |
|---|---|---|
| G01J 1/42 | (2006.01) | |
| G01J 3/28 | (2006.01) | |
| G01J 3/44 | (2006.01) | |
| G01J 3/10 | (2006.01) | |
| G01J 3/02 | (2006.01) | |
| G01N 21/64 | (2006.01) | |

(52) U.S. Cl.
CPC ................ *G01J 3/28* (2013.01); *G01J 3/4406* (2013.01); *G01J 3/10* (2013.01); *G01J 3/0208* (2013.01); *G01N 21/64* (2013.01)

(58) Field of Classification Search
CPC .................................................. G01N 2021/62
USPC ........................................................ 250/372
See application file for complete search history.

(56) References Cited

U.S. PATENT DOCUMENTS 4,715,715 A 12/1987 Howarth et al.
5,642,189 A 6/1997 Alguard
(Continued)

FOREIGN PATENT DOCUMENTS

CN 203069738 U 7/2013
JP 04340441 11/1992
(Continued)

OTHER PUBLICATIONS

Ribes et al., "Reflected-light, photoluminescence and OBIC imaging of solar cells using a confocal scanning laser MACROscope/microscope," 1996, Solar Energy Materials and Solar Cells, vol. 44, pp. 439-450.*

(Continued)

*Primary Examiner* — Kiho Kim
(74) *Attorney, Agent, or Firm* — Tim Tingkang Xia, Esq.; Morris, Manning & Martin, LLP

(57) ABSTRACT

A material aging test apparatus and method thereof are provided. The aging apparatus includes a pulsed laser, a beam expansion assembly, a platform, and a spectrum analyzer. The pulsed laser is used for transmitting a first beam. The beam expansion assembly is used for converting the first beam into a second beam and projecting the second beam onto an object. The platform is used for carrying the object. The spectrum analyzer is used for measuring the spectral response which is generated from the object by the projection of the second beam.

17 Claims, 5 Drawing Sheets

(56) References Cited

U.S. PATENT DOCUMENTS

| | | | |
|---|---|---|---|
| 6,626,052 B1 | 9/2003 | Martin et al. | |
| 7,038,196 B2 | 5/2006 | Scott et al. | |
| 7,123,363 B2 * | 10/2006 | Puttappa et al. | 356/450 |
| 7,630,421 B2 * | 12/2009 | Kobayashi et al. | 372/29.012 |
| 8,274,652 B2 * | 9/2012 | Urano et al. | 356/237.4 |
| 2008/0191137 A1 * | 8/2008 | Poteet et al. | 250/338.1 |
| 2010/0005911 A1 | 1/2010 | Scott et al. | |
| 2011/0241719 A1 | 10/2011 | Shr et al. | |
| 2011/0284769 A1 * | 11/2011 | Matsui et al. | 250/459.1 |

FOREIGN PATENT DOCUMENTS

| | | |
|---|---|---|
| JP | 2004170407 | 6/2004 |
| TW | 201135263 A | 10/2011 |

OTHER PUBLICATIONS

Hanoka, J. I. et al., Accelerated Testing of an Encapsulant for PV Modules, Conference Record of the Twenty-Ninth IEEE, pp. 1565-1567, 2002, Photovoltaic Specialists Conference, 2002.

French, R. H. et al., Optical Properties of Materials for Concentrator Photovoltaic Systems, 34th IEEE, Potovoltaic Specialists Conference (PVSC), 2009, pp. 000394-000399, 2009.

Kojima, Takeshi et al., The Evaluation of Accelerated Test for Degradation a Stacked a-Si Solar Cell and EVA Films, Solar Energy Materials & Solar Cells, pp. 119-123, 2004.

Jin, Jing et al., UV Aging Behaviour of Ethylene-Yinyl Acetate Copolymers (EVA) With Different Vinyl Acetate Cotents, Polymer Degradation and Stability, pp. 725-732, 2010.

Pern, John et al., Module Encapsulation Materials, Processing and Testing, APP International PV Reliability Workshop, National Renewable Energy Laboratory, Dec. 4, 2008-Dec. 5, 2008.

Pern, F. J., Luminescence and Absorption Characterization of Ethylene-Vinyl Acetate Encapsulant for PV Modules Before and After Weathering Degradation, Polymer Degradation and Stability 1993, pp. 125-139, 41, Elsevier Science Publishers Ltd., Golden, CO.

Pern, F.J. et al., Photothermal Stability of Encapsulated Si Solar Cells and Encapsulation Materials Upon Accelerated Exposures, Solar Energy Materials & Solar Cells, 2000, pp. 153-188, 61, Elsevier Science Publishers Ltd., Golden, CO.

Holley, William H. et al., UV Stability and Module Testing of Non-Browning Experimental PV Encapsulants, IEEE 1996, pp. 1259-1262, Enfield, Connecticut.

Intellectual Property Office, Ministry of Economic Affairs, R.O.C., "Notice of Allowance", Dec. 15, 2014, Taiwan.

* cited by examiner

MATERIAL AGING TEST APPARATUS AND METHOD THEREOF

CROSS-REFERENCE TO RELATED APPLICATIONS

This application also claims priority to Taiwan Patent Application No. 102127796 filed in the Taiwan Patent Office on Aug. 2, 2013 and Taiwan Patent Application No. 101134832 filed in the Taiwan Patent Office on Sep. 21, 2012, the entire content of which is incorporated herein by reference.

TECHNICAL FIELD

The present disclosure relates to a test apparatus and method thereof, and more particularly, to a material aging test apparatus and method.

BACKGROUND

Solar energy is an affordable, inexhaustible and clean energy that will have huge longer-term benefits when comparing to the pollution and shortage of fossil energy. Among all the practical applications of solar energy, solar cell, being an electrical device that converts the energy of light directly into electricity by the photovoltaic effect, is becoming an important building block for future alternative energy program.

Generally, solar cells that are designed for long-term outdoor usage would be made of materials with good ability to withstand the effects of wind, rain, or sun and to retain its appearance and integrity, i.e., it would be designed with good weather resistance. When it comes to solar cell and also its package materials that are used to operate under the exposure of sunlight for a considerable long period of time, the ability to resist ultraviolet is one of the factors to be considered as ultraviolet is one of the causes of material degradation.

In a condition when a material aging test is performed using man-made light source, such as xenon lamp, ultraviolet lamp whichever capable of simulating solar light illumination, however under the restriction of their operation modes, such man-made light sources are generally large-area light sources that can project large-area uniform output upon a sample object, but with weaker illuminance per unit area. Under the circumstance, one way for increasing the speed of aging is to increase the intensity of the light sources used in the aging test. Nevertheless, the light source that can project beam with high intensity can likely cause the sample to overheat, which is going to affect the final result of the aging test. Moreover, since most light sources that are currently used in the aging test are designed for large-area aging, they may not be used for focusing their projection only on a specific area of a sample so that different areas of the sample may not be exposed by light sources of different illuminances. In addition, most aforesaid light sources that are currently used in the aging test emit beams within a specific wavelength range, that they might not be able to be conditionally fine tuned for enabling the same to produce a beam of a specific wavelength.

Thereafter, a spectral measurement is performed upon the sample after aging test so as to be used as the base for adjusting and controlling aging test parameters. For the manufacturers of related arts, the aging test apparatus and the spectrum measurement apparatus are two devices that are generally independent of each other as the light sources suitable for the aging test is different from those suitable for the spectral measurement. Therefore, in most cases, the sample after completing the aging test would be removed from the aging test apparatus and transported to a test platform of an independent spectrum measurement apparatus.

Therefore, it may be in need of an apparatus and method with enhanced aging test efficiency that are able to perform a spectral measurement simultaneously with the proceeding of an aging test.

SUMMARY

The present disclosure provides a material aging test apparatus including a pulsed laser, a beam expansion assembly, a platform, and a spectrum analyzer. The pulsed laser is used for transmitting a first beam. The beam expansion assembly is used for converting the first beam into a second beam and projecting the second beam onto an object. The platform is used for carrying the object. The spectrum analyzer is used for measuring the spectral response which is generated from the object by the projection of the second beam.

The present disclosure provides a material aging test method. The method includes the following steps. Projecting a first beam from a pulsed laser to a beam expansion assembly. Converting the first beam into a second beam by the beam expansion assembly while projecting the second beam onto an object for a specific period of time. During the specific period of time, using a spectrum analyzer to measure the spectral response generated from the object by the projection of the second beam.

Further scope of applicability of the present application will become more apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given herein below and the accompanying drawings which are given by way of illustration only, and thus are not limitative of the present disclosure and wherein.

DETAILED DESCRIPTION

Figure 1:
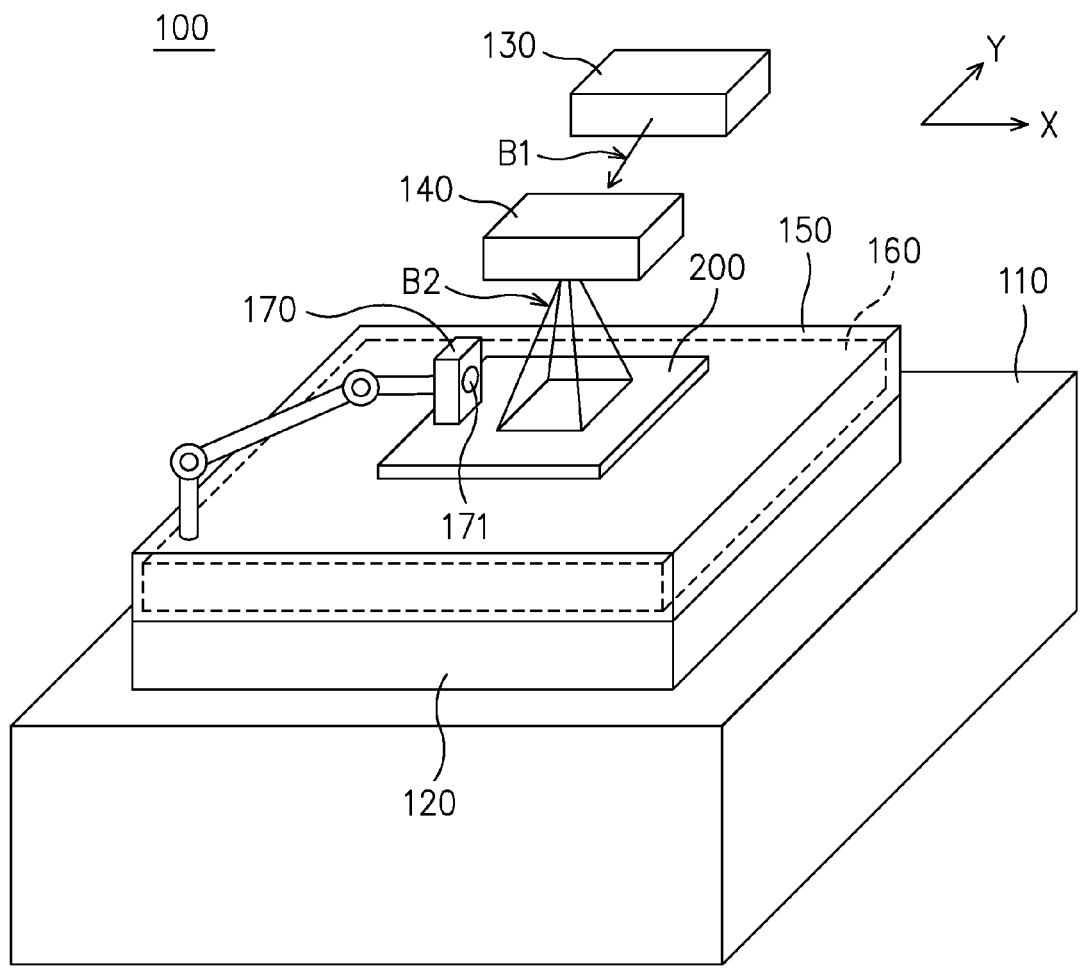
FIG. 1 is a schematic diagram showing a material aging test apparatus according to an embodiment of the present disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Please refer to FIG. 1, which is a schematic diagram showing a material aging test apparatus according to an embodiment of the present disclosure. As shown in FIG. 1, a material aging test apparatus 100 is used for performing an aging test upon an object 200 for evaluating the weather resistance of the object. The material aging test apparatus 100 includes a base 110, a platform 120, a pulsed laser 130, a beam expansion assembly 140 and a spectrum analyzer 170. In this embodiment, the base 110 is a granite base that is provided for the platform 120, the pulsed laser 130, the beam expansion assembly 140 and the spectrum analyzer 170 to mount thereon. In addition, the platform 120 is a XY-axes movable platform that is used for carrying the object 200 while enabling the object 200 to move with the movement of the platform 120, whereas the beam expansion assembly 140 is arranged at a position above the object 200 and the platform 120 for allowing a beam emitted from the pulsed laser 130 to project onto the object 200 carried on the platform 120 through the conversion of the beam expansion assembly 140. Moreover, the material aging test apparatus 100 further has a panel 150 and a temperature control module 160 that are both being disposed on the platform 120, in which the panel 150 is provided for fixing the object 200 thereon by a means of vacuum suction, and the temperature control module 160 is equipped with a water-cooling circuit that can be used for cooling the object 200 on the panel 150.

Operationally, the pulsed laser 130 is used for providing a first beam B1 to the beam expansion assembly 140, where the first beam is converted into a second beam B2 so as to be projected onto the surface of the object 200. It is noted that both the power and the wavelength of the first beam B1 is adjustable. In this embodiment, the pulsed laser 130 is designed to generate the first beam B1 with a wavelength ranged between 280 nm to 400 nm, whereas consequently the wavelength of the second beam B2 is also ranged between 280 nm to 400 nm, whichever is corresponding to UV light that is most effective for material degradation and aging.

In this embodiment, the pulsed laser 130 is a short pulsed laser with a pulse width smaller than 1 μs, and a pulse repetition rate larger than or equal to 10 Hz, by that a uniform laser beam can be converted into a periodic high-energy pulsed laser beam. Therefore, the object 200 is being illuminated by a periodic high-energy illumination for enable an intense aging effect upon the object 200, but with low cumulative energy.

For instance, when the object 200 is substantially a solar cell module and the pulsed laser is featured by a pulse width of 5 ns and a pulse repetition rate of 10 Hz, the average power density of the second beam B2 that is being projected onto the object 200 via the beam expansion assembly 140 can be ranged between 10 kw/$m^2$ and 0.1 kw/$m^2$ that is adjusted according to different expansion areas. However, by the characteristic of the pulsed laser 130, the instance illuminance on the object 200 can achieve 20 Mkw/$m^2$ to 0.2 Mkw/$m^2$, and thereby, the aging effect of the solar cell module can be accelerated but without causing any melting or tempering to the solar cell module. Similarly, when the object 200 is made of a polymer material, the average power density of the second beam is ranged between 5 kw/$m^2$ and 0.1 kw/$m^2$ that also can accelerate the aging effect without causing any damage to the polymer material.

Except for the feature of instantaneity and high power density, the energy of the pulsed laser being projected on the object 200 is not cumulative that is different from those continuous light sources, i.e. the temperature of the object 200 will not be raised continuously by the projection of the second beam. Thereby, the impact of thermal effect upon the aging test of the object 200 will be greatly reduced. In another word, it is quite sufficient to control the temperature of the object 200 that is being aged in the material aging test apparatus 100 simply by the use of the temperature control module 160 disposed on the panel 150. In this embodiment, the temperature control module 160 is able to control the temperature of the object 200 to be maintained in a range between 10° C. and 60° C. Thereby, not only the aging effect can be prevented from being adversely affected by heat accumulation, but also the object can be prevented from being damaged by melting or tempering.

Figure 2:
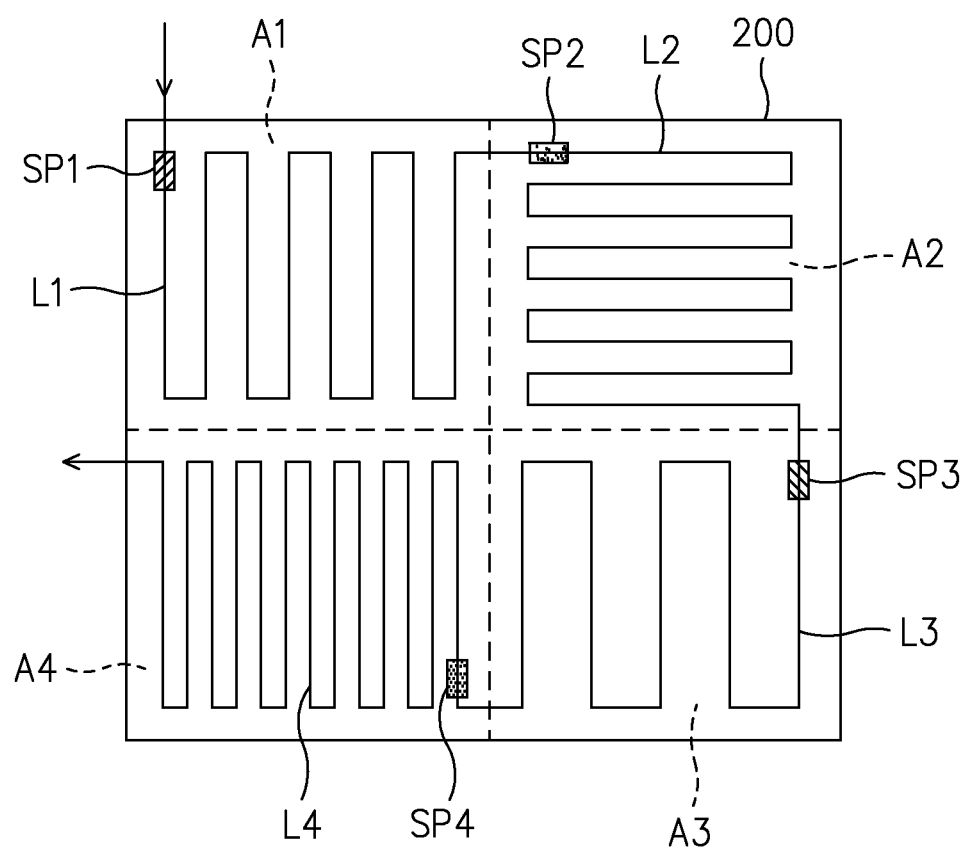
FIG. 2 is a schematic diagram showing a moving trajectory of a light spot on an object of FIG. 1 by the projection of a second beam.

Please refer to FIG. 2, which is a schematic diagram showing a moving trajectory of a light spot on an object of FIG. 1 by the projection of a second beam. In this embodiment, a user is able to control the moving trajectory of a light spot on the object 200 that is caused by the projection of the second beam B2 by enabling the object 200 to be brought along to move with the movement of the platform 120, and moreover, the moving trajectory, power, and wavelength range of the second beam B2 are enabled to be adjusted according to required test conditions.

In an embodiment that the surface of the object 200 is divided into four areas, i.e. A1 to A4, and the second beam B2 is enabled to scan respectively through the four areas A1 to A4 via different optical trajectories, and simultaneously enabling the power, the wavelength, and the projection area of the second beam B2 to change with the changing of the optical trajectory. As shown in FIG. 2, the light spot SP1 formed on the object 200 by the second beam B2 is scanning and travelling via the optical trajectory L1, whereas similarly, the light spots SP2, SP3, SP4 are scanning respectively in the area A2, A3, A4 via the optical trajectories L2, L3, L4. The density of the optical trajectories L1 to L4 existed in different aging areas, i.e. A1 to A4, are different from one another. Thereby, it is possible for a user to conduct different aging tests on one object 200 using different light exposure conditions, so that the user is able to obtain aging resistance parameters relating to the object 200 in a more effective manner. In addition, by adjusting the wavelength of the pulsed laser 130, a specific aging effect on the object 200 that is resulted from a specific wavelength can be selected, and thereby, a user is able to construct a relative relationship between material characteristics of the object 200 and their corresponding wavelengths.

Figure 3:
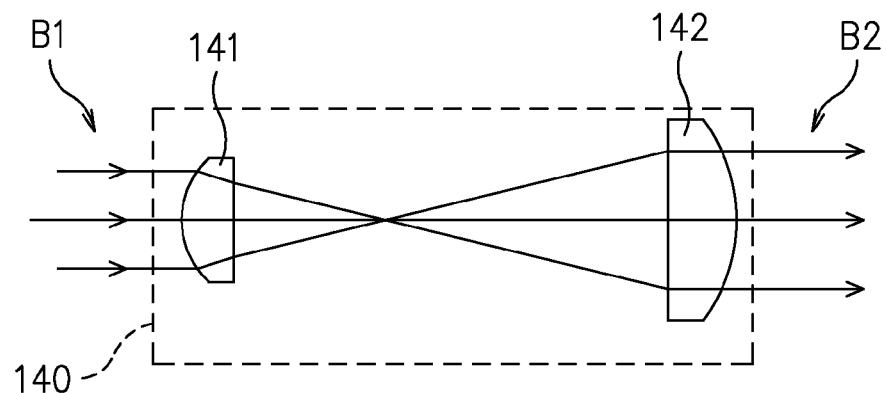
FIG. 3 is a schematic diagram showing a beam expansion assembly according to an embodiment of the present disclosure.

For achieving the aforesaid effect, the first beam B1 of the pulsed laser 130 is projected to the beam expansion assembly 140, where it is being converted into a second beam B2 so as to be projected onto the object 200, forming the required light spot. Please refer to FIG. 3, which is a schematic diagram showing a beam expansion assembly according to an embodiment of the present disclosure. As shown in FIG. 3, the beam expansion assembly 140 is composed of a plurality of optical parts or lenses, such as the lenses 141 and 142 shown in FIG. 3, by that the spot of the first beam B1 can be expanded and shaped into required figure while allowing the spot area of the second beam B2 to be larger than the spot area of the first beam B1. As shown in FIG. 2, there are four spots SP1~SP4 with areas larger than 1 cm$^2$ that are being formed on the object 200 of 20 cm$^2$, while allowing the four spots SP1~SP4 to scan the object 200 via different optical trajectories disclosed in FIG. 2 so as to accelerate the aging of the object 200. In addition, after expansion, the energy per unit area of the second beam B2 is smaller than the energy per unit area of the first beam B1, so that the object 200 can be prevented from overheating by the projection of the second beam B2.

Figure 4:
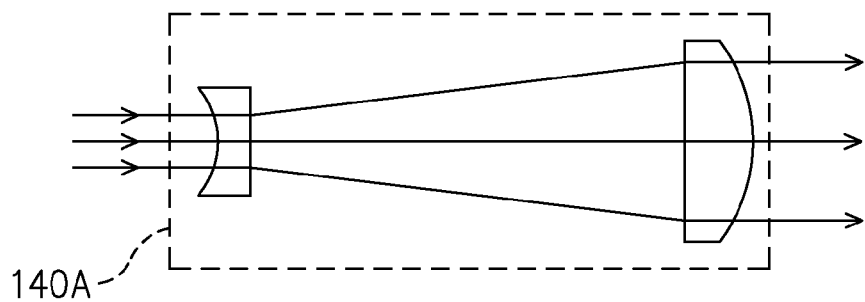
FIG. 4 is a schematic diagram showing a beam expansion assembly according to another embodiment of the present disclosure.
Figure 5:
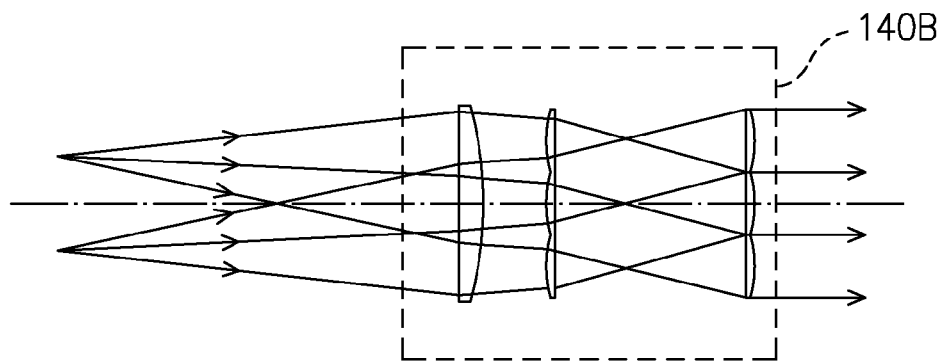
FIG. 5 is a schematic diagram showing a beam expansion assembly according to further another embodiment of the present disclosure.

There is no restriction to the assembly and construction of the beam expansion assembly 140, only if it is able to expand and shape the first beam B1 from the pulsed laser 130. Please refer to FIG. 4, which is a schematic diagram showing a beam expansion assembly according to another embodiment of the present disclosure. In the embodiment shown in FIG. 4, the beam expansion assembly 140A is a Galilean beam expander, which is structurally different from the Keplerian beam expander shown in FIG. 3, but can achieve the same expansion effect. Please refer to FIG. 5, which is a schematic diagram showing a beam expansion assembly according to further another embodiment of the present disclosure. In FIG. 5, the beam expansion assembly 140B is able to perform a beam expansion operation on two beam simultaneously. Consequently, a user is able to define the shape and size of a light spot that is to be projected on the object 200 according to the figure and size of the object 200 by the use of such beam expansion assembly.

Figure 6:
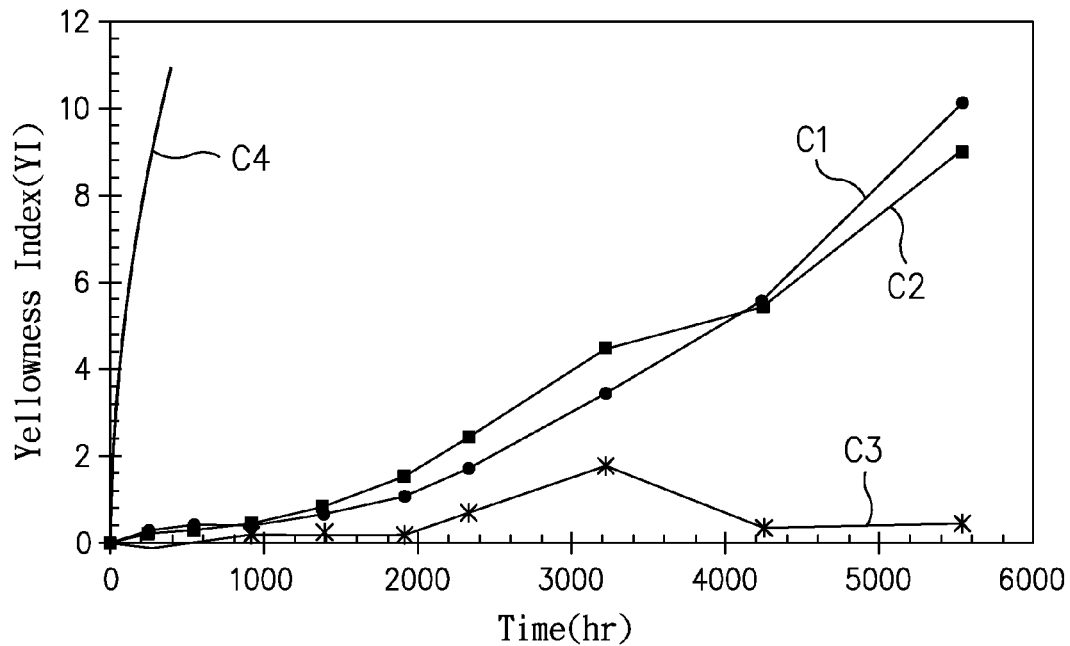
FIG. 6 is a schematic diagram showing curves of yellow index that are respectively the result of an aging test using a pulsed laser as its light source and the results of other aging tests using conventional light sources.

Please refer to FIG. 6, which is a schematic diagram showing curves of yellow index that are respectively the result of an aging test using a pulsed laser as its light source and the results of other aging tests using conventional light sources. In FIG. 6, the curves C1~C3 represents the change of yellowness index of three different aging tests performed on three different objects under the same condition and using a conventional xenon lamp. For the objects represented by curves C1 and C2, both required to be illuminated by 5600 hours so as to enable their corresponding yellowness indexes to approach 10. However, for the curve C4 which represents the result of an aging test using a pulsed laser as its light source for projecting the material of curve C1, the yellowness index can achieve 10 in 400 hours. Therefore, the pulsed laser is proven to be an effective light source for accelerate the aging effect.

It is noted that the curves C1~C3 are obtained from prior researches, whereas the objects used in curves C1~C3 are made of same materials, but using different formulas. As for the prior researches indicated above is a report of John Pern, Ph.D. that is disclosed in APP International PV Reliability Workshop at China, Shanghai at Dec. 4 and 5,2008.

Figure 7:
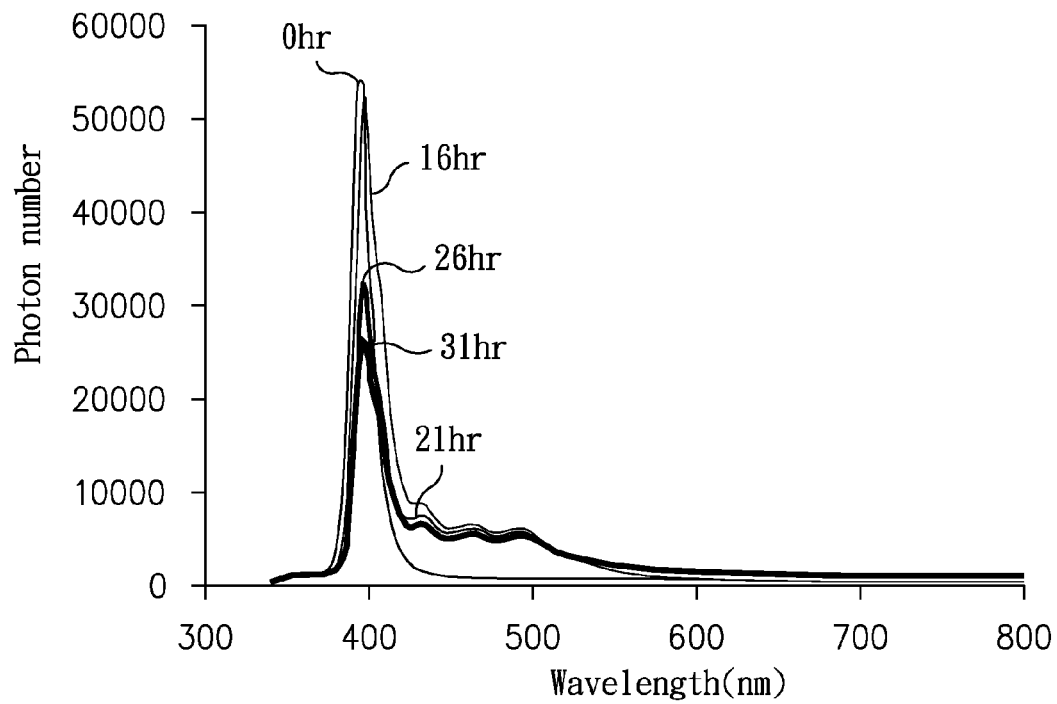
FIG. 7 is a spectral response diagram of an object depicting the time variation of photon number.
Figure 8:
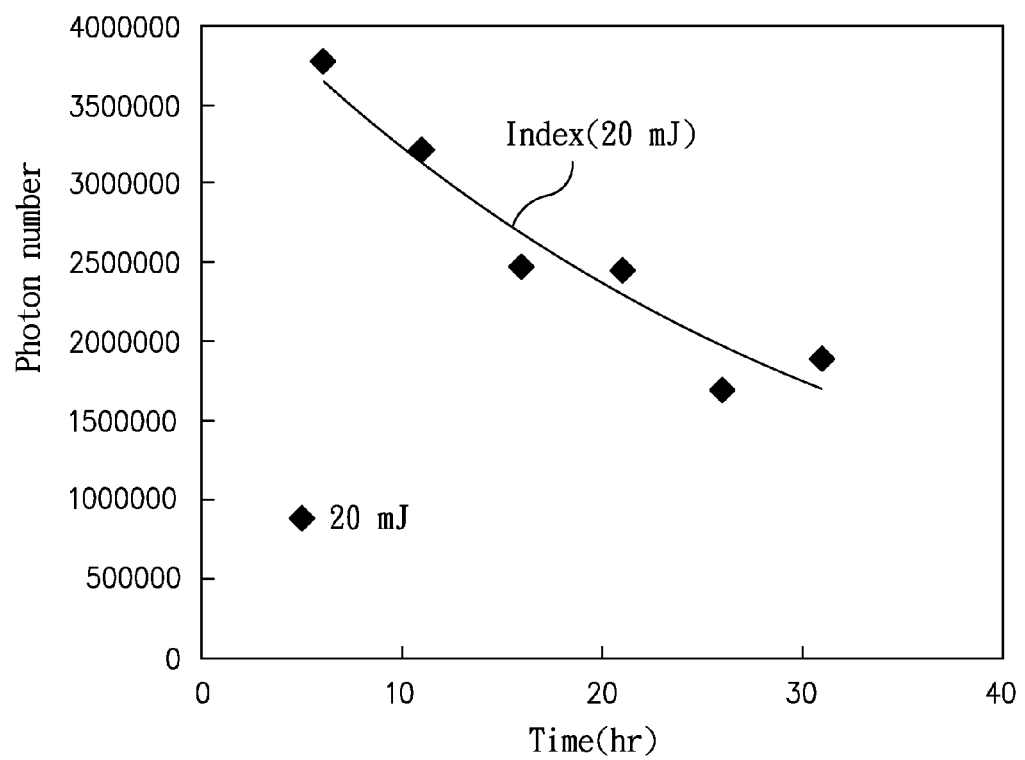
FIG. 8 is a diagram showing the integral of spectral response of FIG. 7.

Please refer to FIG. 1 for disclosing the operation of the spectrum analyzer 170. When the object 200 is illuminated by the second beam B2, the object 200 can be excited to emit a fluorescent light that can be measured by the spectrum analyzer 170. It is noted that after the laser energy of the second beam B2 is being absorbed by the object 200, the molecules of the material are excited into electronic transition so as to emit a fluorescent light accordingly, whereas the wavelength of the fluorescent light can be different when the transition state is different, and the aging degree of the object 200 is related to the degradation of the fluorescent light. Please refer to FIG. 7, which is a spectral response diagram of an object depicting the time variation of photon number. When the object 200 is being aged, the spectrum analyzer is enabled to perform a spectral response measurement every other time, that is, the spectral response is measured at 0 hr., 16 hr., 21 hr., 26 hr., and 31 hr. The spectral response of the object is decreasing with the increasing of time, which can be even more obvious in the integration of FIG. 7. Please refer to FIG. 8, which is a diagram showing the integral of spectral response of FIG. 7. In FIG. 8, the energy projected on the object is 20 mJ. Accordingly, during the projection of the second beam B2 on the object, the spectrum analyzer 170 that is designed to work cooperatively with a filter 171 is able to measure the spectral responses of the object 200 that is caused by the projection of the second beam B2.

The spectrum analyzer 170 can be turned on along with the activation of the material aging test apparatus 100, or it can be turned on at the time when the pulsed laser is first being enabled to emit the first beam B1, but it is not limited thereby, only if the spectrum analyzer 170 starts to measure the spectral responses before the object 200 is being illuminated by the second beam B2. That is, the spectrum analyzer 170 measures the spectral response from the beginning of the fluorescent spectral response of object 200 until no spectral response. More specifically, the spectrum analyzer 170 measures the spectral response of the object 200 from the time when the second beam B2 starts to be projected onto the object 200 for exciting the object 200 to emit fluorescent light, through the time when the spectral response of the object 200 is at a maximum value, to the time when the spectral response of the object 200 is at a minimum value. The time when the spectral response of the object 200 is at the minimum value is the time when there is no spectral response from the object 200. The spectrum analyzer 170 is not needed to be turned off after the spectral response of the object 200 is at the minimum value. In an embodiment, the spectral response of the object 200 is the spectral response of the fluorescent light emitted from the object 200. In an embodiment when the object 200 is a solar cell module, the related fluorescent light is ranged between 400 nm~800 nm. As for the filter 171, its type can be selectively changed with the changing of the object 200 being tested. For instance, when the spectrum analyzer 170 adopts a visible light ranged between 350 nm~1000 nm for measurement, the related filter 171 can be a visible light filter of 380 nm~700 nm so as to block the high-energy short-wavelength light under 380 nm while allowing the light ranged between 380 nm~720 nm to pass through. On the other hand, if the pulsed laser 130 is replaced by a white light source, there will be no need for the filter.

The present disclosure also provides a material aging test method, which comprises the steps of: projecting a first beam B1 from a pulsed laser 130 to a beam expansion assembly 140; enabling the first beam B1 to be converted into a second beam B2 by the beam expansion assembly 140 while projecting the second beam B2 onto an object 200 lasting for a specific period of time; and during the specific period of time, using a spectrum analyzer 170 to measure the spectral response generated from the object 200 by the projection of the second beam B2.

According to the foregoing embodiments, the material aging test apparatus adopts a pulsed laser as its light source, whereas the cross area of the beam emitted from the pulsed laser is adjusted by a beam expansion assembly in a manner that the average illuminance per unit area is reduced so that the object being tested can be illuminated by a periodic high-energy illumination for enable an intense aging effect upon the object, but with low cumulative energy. Thereby, the shortcomings of the conventional aging apparatuses that are generally resulted from the use of conventional light sources can be overcome. Moreover, since the pulsed laser is able to provide regional illumination to the object being tested, a user is able to control the moving trajectory of a light spot on the object by enabling the object to be brought along to move with the movement of the platform, the pulsed laser is able to illuminate the object using the second beam B2 of different moving trajectory, power and wavelength range. Thereby, it is possible for a user to conduct different aging tests on one object using different light exposure conditions, so that the user is able to obtain aging resistance parameters relating to the object in a more effective manner. In addition, the material aging test apparatus of the present disclosure adopts a pulsed laser as its light source, whereas a spectral response measurement is performed simultaneously in real time during the aging process so as to be used as a base for evaluation the aging of the material.

To sum up, the material aging test apparatus of the present disclosure is able to perform a aging process and a spectral response measurement simultaneously using the same light source, and the object to be tested in placed on a multi-axial moveable platform so that the object can be brought along to move with the movement of the platform without having to actually pick up the object and move it to another location.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

What is claimed is:

1. A material aging test apparatus, the apparatus comprising:
    a pulsed laser, used for providing a first beam;
    a beam expansion assembly, used for converting the first beam into a second beam and projecting the second beam onto an object;
    a platform, used for carrying the object; and
    a spectrum analyzer, used for measuring a spectral response generated from the object by the projection of the second beam,
    wherein the object is a solar cell, and an average power density of the second beam is ranged between 10 kw/m$^2$ and 0.1 kw/m$^2$.

2. The material aging test apparatus of claim 1, further comprising:
    a filter, disposed at a position between the object and the spectrum analyzer.

3. The material aging test apparatus of claim 1, wherein the platform is a movable platform, used for carrying the object to move with movements of the platform so as to enabling the second beam to scan the object via at least one optical trajectory.

4. The material aging test apparatus of claim 3, wherein the object includes a plurality of aging areas, and each aging area is scanned by the second beam via more than one optical trajectory in a principle that density of the optical trajectories existed in different aging areas are different from one another.

5. The material aging test apparatus of claim 1, wherein a power of the first beam is adjustable.

6. The material aging test apparatus of claim 1, wherein a wavelength of the first beam is adjustable.

7. The material aging test apparatus of claim 6, wherein an adjustable wavelength range of the first beam is ranged between 280 nm and 400 nm.

8. The material aging test apparatus of claim 1, wherein a pulse width of the pulsed laser is smaller than 1 μs, and a pulse repetition rate of the pulsed laser is not smaller than 10 Hz.

9. The material aging test apparatus of claim 1, wherein an area of the object that is covered by the projection of the second beam is larger than 1 cm$^2$.

10. The material aging test apparatus of claim 1, further comprising:
    a temperature control module, for controlling the temperature of the platform at a position thereof for carrying the object.

11. The material aging test apparatus of claim 10, wherein an adjustable temperature range of the platform is between 10° C. to 60° C.

12. The material aging test apparatus of claim 1, wherein the object is capable of being excited to emit a fluorescent light by the projection of the second beam.

13. A material aging test apparatus, the apparatus comprising:
    a pulsed laser, used for providing a first beam;
    a beam expansion assembly, used for converting the first beam into a second beam and projecting the second beam onto an object;
    a platform, used for carrying the object; and
    a spectrum analyzer, used for measuring a spectral response generated from the object by the projection of the second beam,
    wherein the object is made of a polymer material, and an average power density of the second beam is ranged between 5 kw/m$^2$ and 0.1 kw/m$^2$.

14. A material aging test method, the method comprising:
    projecting a first beam from a pulsed laser to a beam expansion assembly;
    converting the first beam into a second beam by the beam expansion assembly while projecting the second beam onto an object for a specific period of time; and
    during the specific period of time, using a spectrum analyzer to measure a spectral response generated from the object by the projection of the second beam,
    wherein the object is a solar cell, and an average power density of the second beam is ranged between 10 kw/m$^2$ and 0.1 kw/m$^2$.

15. The material aging test method of claim 14, wherein the specific period of time used by the spectrum analyzer for measuring the spectral response of the object is from a time when the second beam starts to be projected onto the object, through a time when the spectral response of the object is at a maximum value, to a time when the spectral response of the object is at a minimum value.

16. The material aging test method of claim 15, wherein the time when the spectral response of the object is at the minimum value is the time when there is no spectral response from the object.

17. The material aging test method of claim 14, wherein the object is capable of being excited to emit a fluorescent light by the projection of the second beam; and the spectrum analyzer is used for measuring the spectral response of the fluorescent light emitted from the object.

* * * * *